United States Patent [19]

Ogura et al.

[11] Patent Number: 4,981,796

[45] Date of Patent: Jan. 1, 1991

[54] MANUFACTURING METHOD OF OPTICALLY-ACTIVE 1,2-DIOLS

[75] Inventors: Masahiro Ogura, Ono; Tadayoshi Shiraishi, Takasago; Hideyuki Takahashi, Kakogawa; Junzo Hasegawa, Akashi, all of Japan

[73] Assignee: Kanegafuchi Kagaku Kogyo Kabushiki Kaisha, Osaka, Japan

[21] Appl. No.: 275,200

[22] Filed: Nov. 23, 1988

[30] Foreign Application Priority Data

Nov. 25, 1987 [JP] Japan .................. 62-296494
Jul. 1, 1988 [JP] Japan .................. 63-165484
Jul. 5, 1988 [JP] Japan .................. 63-167197

[51] Int. Cl.$^5$ ................................ C12P 7/22
[52] U.S. Cl. .................. 435/156; 435/158; 435/280; 435/911; 435/921; 435/938
[58] Field of Search ............. 435/156, 158, 280

[56] References Cited

FOREIGN PATENT DOCUMENTS 3336051 4/1985 Fed. Rep. of Germany .

OTHER PUBLICATIONS

Nippon Kagaku Zasshi, vol. 91, p. 265 (1970).
Chemical Abstracts, vol. 105, p. 77,513 (1986).
Journal of Organic Chemistry, vol. 51, p. 25 (1986).

*Primary Examiner*—Herbert J. Lilling
*Attorney, Agent, or Firm*—Sughrue, Mion, Zinn, Macpeak and Seas

[57] ABSTRACT

A process of manufacturing optically active (S)-1,2-diols, wherein (R)-1,2-diols represented by the general formula [I]

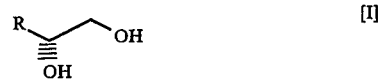

(where: R represents a substituted or unsubstituted alkyl group, alkenyl group, aryl group or aralkyl group) or a mixture of diols of the general formula [I] and (S)-1,2-diols represented by the general formula [II]

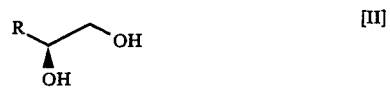

(Where: R represents the same as above) having an opposite configuration to the general formula [I] is subjected to the action of a microorganism capable of selectively metabolizing the diols of the general formula [I], or capable of converting the diols of the general formula [I] into the diols of the general formula [II], or having the both capabilities, and the formed and accumulated (S)-1,2-diols of the general formula [II] is collected. According to the present invention, optically active (S)-1,2-diols can be produced commercially and advantageously.

6 Claims, No Drawings

MANUFACTURING METHOD OF OPTICALLY-ACTIVE 1,2-DIOLS

BACKGROUND OF THE INVENTION

1. Field of the Invention

The present invention relates to a novel method of manufacturing optically-active 1,2-diols useful materials for synthesis of physiologically-active compounds having specific uses in the fields of drugs and agrichemicals.

2. Description of the Prior Art

As to the method of synthesizing optically-active 1,2-diols, a method synthesizing (S)-1,2-propanediol, (S)-1,2-pentanediol, (S)-1,2-hexanediol with an amino acid such as L-alanine as starting material through alpha-hydroxy acid as intermediate is known but this method needs an expensive reducing agent and can hardly be called a commercial method ("Nippon Kagaku Zasshi," vol. 91, p. 265, 1970).

Meanwhile, as a method of manufacturing optically-active 1,2-diols by the use of microorganisms, a method of manufacturing (R)-1,2-propanediol from glucose et cetera using microorganisms of Clostridium genus is known [West German patent DE No. 3336051 (1985), Chemical Abstract; vol. 105, p. 77, 513 (1986)]. Whitesides et. al. reported that they had used glycerol dehydrogenase obtained from a microorganism of Cellulomonas genus and could thus obtain (R)-1,2-propanediol and (R)-1,2-butanediol from 1-hydroxy-2-propanone and 1-hydroxy-2-butanone, respectively [Journal of Organic Chemistry (J. Org. Chem.), vol. 51, p. 25 (1986)].

As examples of biochemical steric inversion cases, the racemization of optically-active compounds by the use of racemiase are well known such as cases involving amino acids, but it is impossible to make any optically-active substance from such racemic compounds by the opposite route.

Thus, all these methods had many problems still to be solved before commercialization of any thereof, and early development of a commercially advantageous method for manufacture of optically-active 1,2-diols has been looked forward to.

SUMMARY OF THE INVENTION

It is a primary object of the present invention to provide a method of manufacturing optically-active 1,2-diols commercially and advantageously.

Other objects and advantages of the present invention will become apparent for those skilled in the art from reading of the detailed description below.

After extensive and intensive studies for accomplishing the aforementioned object of developing a method of commercially manufacturing optically-active 1,2-diols, the present inventors discovered that optically-active (S)-1,2-diols can be manufactured efficiently with racemic compounds of (R,S)-1,2-diols or (R)-1,2-diols as starting materials by microbiological reactions and could thus completed the present invention.

As such microbiological reactions, there may be included a metabolic decomposition reaction in which (R)-1,2-diols are decomposed with priority, a conversion reaction in which (R)-1,2-diols are converted by steric inversion into (S)-1,2-diols and an overall reaction representing combinations of these approaches. Such classification of modes of reaction is, however, of no particular importance, and the present invention generally relates to a method of manufacturing (S)-1,2-diols with a mixture of (R) and (S)-1,2-diols such as a racemic compound or (R)-1,2-diol as material by means of the aforementioned microbiological reaction in which (S)-1,2-diols are selectively caused to remain or increase to be collected at the end of the process.

DETAILED DESCRIPTION OF THE INVENTION

The present invention relates to a method of manufacturing optically-active (S)-1,2-diols, wherein (R)-1,2-diols having a configuration represented by the general formula [I]

(where: R represents a substituted or unsubstituted alkyl group, alkenyl group, aryl group or aralkyl group) or a mixture of diols of the general formula [I] and (S)-1,2-diols represented by the general formula [II]

(Where: R represents the same as above) having an opposite configuration with respect to the general formula [I] is subjected to action of a microorganism capable of selectively metabolizing the diols of the formula [I] or another microorganism capable of converting by steric inversion into diols of the formula [II] or a still another microorganism having both of these capabilities and the formed and accumulated diols of the formula [II] is collected.

The present invention will be described below in greater detail.

As substrates usable in the present invention, 1,2-diols of the aforementioned general formula (1) or a mixture (the so-called racemic compounds) of 1,2-diols of the general formula (1) and (2) may be used. "R" may include unsubstituted alkyl groups such as ethyl group, propyl group, isopropyl group, butyl group, isobutyl group, pentyl group, hexyl group and cyclohexyl group; substituted alkyl groups such as methylthiomethyl group and methoxymethyl group; alkenyl group such as vinyl group and allyl group; aryl group such as phenyl group, tolyl group and methoxyphenyl group; and aralkyl group such as benzyl group and phenethyl group.

As microorganisms applicable to the method of the present invention, there may be included those capable of selectively metabolizing (R)-1,2-diol or capable of converting (R)-1,2-diol into (S)-1,2-diol or having both capabilities, but enumerated below are typical examples. Namely, microorganisms belonging to genera Arthroascus, Candida, Debaryomyces, Endomyces, Guilliermondells, Hansenula, Kluyveromyces, Lodderomyces, Pichia, Rhodotorula, Saccharomyces, Stepohanoascus, Trigonopsis, Trichosporon, Serratia, Klebsiela, Enterobacter, Erwinia, Hafnia, Achromobacter, Agrobacterium, Bacillus, Cellulomonas, Citrobacter, Corynebacterium, Escherichia, Microbacterium, Pseudomonas, Amauroascus, Arxiella, Backusella, Botryotinia, Cephalosporium, Circinella, Dicranidion, Emericellopsis, Fusarium, Gibberella, Gloeophyllum, Laetiporus, Pestalotia, Pholiota, Pleurotus, Gongranella, Rhincoladiella, Rhizopus, Syncephalastrum, Tyromyces and Zygosporium may be exemplified. These may be used alone as well as in combination.

Although these microorganisms are all capable of metabolizing (R)-1,2-diols with priority, some of them, for example, those belonging to genera Arthroascus, Candida, Debaryomyces, Endomyces, Guilliermondella, Lodderomyces, Pichia, Stephanoascus, Backusella, Emericellopsis, Fusarium, Gibberella, Pholiota, Syncephalastrum, Tyromyces, Zygosporium and Gongranella are particularly capable of converting (R)-1,2-diols into (S)-1,2-diols having an opposite configuration as shown in the general formula [II].

As concrete examples of microorganisms applicable to the method of the present invention, there may be exemplified, among others, *Arthroascus javanensis* IFO 1848, *Candida parapsilosis* IFO 0585, *Candida maltosa* ATCC 20275, *Debaryomyces hansenii* IFO 0564, *Endomyces tetrasperma* CBS 765.70, *Guilliermondella selenospora* IFO 1850, *Hansenula holstii* IFO 0980, *Kluyveromyces fragilis* IFO 0288, *Lodderomyces elongisporus* IFO 1676, *Pichia toletana* IFO 0950, *Rhodotorula minuta* IFO 0387, *Saccharomyces bailii* IFO 0468, *Stephanoascus ciferrii* IFO 1854, *Trigonopsis variabilis* IFO 0671, *Trichosporon cutaneum* IFO 0598, *Serratia marcescens* IFO 12648, *Klebsiela pneumoniae* IFO 3319, *Enterobacter cloacae* IFO 12937, *Erwinia herbicola* IFO 12686, *Hafnia alvei* IFO 3731, *Achromobacter xerosis* IFO 12668, *Agrobacterium radiobacter* IFO 13259, *Bacillus pumilus* IFO 3813, *Cellulomonas flavigena* IFO 3748, *Citrobacter freundii* IFO 12681, *Corynebacterium xerosis* IFO 12684, *Escherichia coli* IFO 3301, *Microbacterium lacticum* IFO 14135, *Pseudomonas chlororaphis* IFO 3904, *Amauroascus reticulatus* IFO 9196, *Arxiella terrestris* IFO 30203, *Backusella circina* IFO 9231, *Botryotina fuckeliana* IFO 9760, *Cephalosporium potronii* IFO 4019, *Circinella mucoroides* IFO 4453, *Dicranidion fragile* IFO 6886, *Emericellopsis glabra* IFO 9031, *Fusarium anguioides* IFO 4467, *Gibberella fujikuroi* IFO 6607, *Gloeophyllum striatum* IFO 6506, *Laetiporus sulphureus* IFO 6432, *Pestalotia conigena* IFO 30315, *Pholiota nameko* IFO 6141, *Pleurotus ostreatus* IFO 6515, *Rhincoladiella anceps* IFO 9448, *Gongranella butleri* IFO 8080, *Rhizopus stolonifer* IFO 4781, *Syncephalastrum nigricans* HUT 1299, *Tyromyces palustris* IFO 30339 and *Zygosporium masonii* IFO 30214.

In practicing the present invention, (S)-1,2-diols can be manufactured with an improved efficiency by using a mutant treated to block metabolism of (S)-1,2-diols.

As to the composition of media for cultivation of these microorganisms, there is no particular limitation if they are normally accepted to be good for growth of such microorganisms, and, for instance, carbon sources may include saccharides such as glucose and sucrose; organic acids such as lactic acid and acetic acid; alcohols such as ethanol, glycerol and 1,2-propanediol and their mixtures; and nitrogen sources may include ammonium sulfate, ammonium phosphate, urea, yeast extract, meat extract, peptone, soybean et cetera. Further, nutrients usually used for cultivation of microorganisms such as inorganic salts and vitamins may be used as necessary properly mixed.

Cultivation of microorganisms may be carried out in a usual way with pH in a range of 4.0–9.5, cultivation temperature in a range of 15°–45° C. and for a period of 10–96 hours under aerobic conditions.

As methods for obtaining optically active 1,2-diols of the general formula [II] by the reaction of (R)-1,2-diols of general formula [I] or racemate of it with microorganisms, there are known, among others, processes of suspending a culture solution resulting from cultivation in the aforementioned manner or cells obtained from such culture solution by centrifugation, filtration etc. in a proper buffer solution, and adding 1,2-diols as material to the resulting cells suspension, and of adding such microorganisms to the medium at the time of starting cultivation. In carrying out the reaction, increase of the reaction velocity is attainable through addition of carbon source such as glucose, glycerol and ethanol. When it is desired to have (R)-1,2-diol only selectively metabolized as well as to have (R)-1,2-diol inverted, it is preferred to control the reaction liquor pH in a range of 4.0–10.0 and the temperature in a range of 15°–40° C. The concentration of the 1,2-diols in the reaction mixture may vary over a wide range (0.1–20% W/V) depending on the enzyme activity of the microorganisms used, but it may be added whole at the beginning of the reaction or in portions as well. The reaction is usually conducted under shaking or stirring and the reaction time ranges from 10 to 120 hours depending on the substrate's concentration, enzyme activity and other conditions.

Quantitative determination of 1,2-diols is feasible by gas liquid chromatography (GLC) by the use of, for example, Shimadzu's FAL-M6% (Shimalite TPA) 50 cm Column at a column temperature of 160°–180° C. and an $N_2$ gas flow rate of 20 ml/min. Measurement of optical purity was done by a suitable method according to the kind of the 1,2-diol in question, for example, high performance liquid chromatography (HPLC) or gas liquid chromatography (GLC), and in some cases the specific optical activity was measured after isolation and refining.

For collecting the optically-active 1,2-diol thus obtained from the reaction liquor, the method generally used for collecting glycols is usable. For instance, the cells may first be eliminated by centrifugation or the like, and then the supernatant may be properly concentrated and extracted with a solvent such as ethyl acetate. The organic layer may be dehydrated by the use of Glauber's salt et cetera and, after removal of the solvent under vacuum, may be refined by vacuum distillation or by silica gel chromatography, and optically-active 1,2-diols can thus be obtained with a high purity.

Hereafter the present invention is explained in greater detail by way of examples but it is to be understood that these are only for illustrative purpose and by no means limit the scope of the invention.

EXAMPLE 1

(A) Medium for yeasts Glucose 4% (% by weight, hereinafter the same), $(NH_4)_2HPO$ 1.3%, $KH_2PO_4$ 0.7%, $MgSO_4.7H_2O$ 800 ppm., $ZnSO_4.7H_2O$ 60 ppm., $FeSO_4.7H_2O$ 90 ppm., $CuSO_4.5H_2O$ 5 ppm., $MnSO_4.4H_2O$ 10 ppm., NaCl 100 ppm., yeast extract 0.3%, pH 7.0.

(B) Medium for bacteria and molds Glucose 2%, meat extract 0.5%, peptone 0.5%, yeast extract 0.3%, pH 7.0.

Each medium of the above composition was prepared using tap water, poured 500 ml each into 2-liter Sakaguchi flasks and these were sterilized for 20 minutes in an autoclave at 120° C.

The medium (A) was inoculated with each of the microorganisms shown in Table 1 and the medium (B) was inoculated with each of the microorganisms shown in Table 2 and Table 3 respectively, and after cultivation under shaking for 24–48 hours at 30° C., 1.5 liters of culture solution was obtained. The culture solution so obtained was centrifuged or filtered to separate the cells and, after rinsing, the cells were suspended in 500 ml of a 0.1M phosphate buffer solution (pH 6.5) and after addition of 5.0 g of (R,S)-1,2-pen-tanediol the suspension was poured into 2-liter Sakaguchi flasks, each flask was shaken at 30° C. for 24–120 hours for the reaction to proceed and the reaction was terminated when not less than 50% of the added substrate was decomposed (decomposition percentage determined by GLC analysis). After termination of the reaction, cells were removed by centrifugation or filtration, the supernatant was concentrated under vacuum to 50 ml and extracted 3 times with 150 ml of ethyl acetate. After dehydration with sodium sulfate anhydride and removal of the solvent under vacuum, this extracted liquor was distilled (98°–102° C./13 mmHg) and colorless oily 1,2-pentanediol was thus obtained $\{[\alpha]_D^{20} -12.8° \sim -16.8°$ (C=1, methanol)$\}$ A part of this 1,2-pentanediol was caused to react with p-toluene sulfonyl chloride in methylene chloride in the presence of pyridine for synthesis of 2-hydroxypentyl-p-toluene sulfonate, this was analyzed by HPLC by the use of Chiral CEL CD (of Nippon Bunko, Ltd.) (eluting solution hexane-isopropanol (97:3), flow rate 0.7 ml/min., detection 254 nm, (S)-isomer was eluted in 50 minutes and (R)-isomer in 45 minutes), and the result of optical purity of (S)-1,2-pentanediol [{(area of (S)-isomer)-(area of (R)-isomer)}/{(area of (S)-isomer)-+(area of (R)-isomer)}×100] is given in Tables 1 through 3, which show that optically-active (S)-1,2-pentanediol was obtained from a racemic 1,2-pentanediol with a high yield.

By the way, none of the microorganisms used was confirmed to have ability to synthesize (R)- and (S)-1,2-pentanediol directly from a hydrogen source such as glucose under the aforementioned conditions.

TABLE 1

| Microorganisms | (S)-1,2-pentanediol | |
|---|---|---|
| | Yield* (%) | Optical purity (% e.e.) |
| Arthroascus javanensis IFO 1848 | 44 | 97 |
| Candida parapsilosis IFO 0585 | 45 | 100 |
| Candida maltosa ATCC 20275 | 47 | 100 |
| Debaryomyces hansenii IFO 0564 | 36 | 96 |
| Endomyces tetrasperma CBS 765.70 | 18 | 99 |
| Guilliermondella selenospora IFO 1850 | 38 | 98 |
| Hansenula holstii IFO 0980 | 48 | 91 |
| Kluyveromyces fragilis IFO 0288 | 41 | 82 |
| Lodderomyces elongisporus IFO 1676 | 46 | 100 |
| Pichia toletana IFO 0950 | 43 | 99 |
| Rhodotorula minuta IFO 0387 | 48 | 88 |
| Saccharomyces bailii IFO 0468 | 42 | 79 |
| Stephanoascus ciferrii IFO 1854 | 40 | 99 |
| Trigonopsis variabilis IFO 0671 | 41 | 96 |
| Trichosporon cutaneum IFO 0598 | 33 | 76 |
| Amauroascus reticulatus IFO 9196 | 33 | 96 |
| Arxiella terrestris IFO 30203 | 30 | 99 |
| Backusella circina IFO 9231 | 35 | 100 |
| Botryotinia fuckeliana IFO 9760 | 37 | 89 |
| Cephalosporium potronii IFO 4019 | 41 | 78 |
| Circinella mucoroides IFO 4453 | 42 | 93 |

TABLE 2

| Microorganisms | (S)-1,2-pentanediol | |
|---|---|---|
| | Yield* (%) | Optical purity (% e.e.) |
| Dicranidion fragile IFO 6886 | 40 | 96 |
| Emericellopsis glabra IFO 9031 | 37 | 100 |
| Fusarium anguioides IFO 4467 | 41 | 100 |
| Gibberella fujikuroi IFO 6607 | 46 | 99 |
| Gloeophyllum striatum IFO 6506 | 45 | 98 |
| Laetiporus sulphureus IFO 6432 | 23 | 91 |
| Pestalotia conigena IFO 30315 | 31 | 86 |
| Pholiota nameko IFO 6141 | 35 | 98 |
| Pleurotus ostreatus IFO 6515 | 27 | 85 |
| Rhincoladiella anceps IFO 9448 | 18 | 93 |
| Rhizopus stolonifer IFO 4781 | 28 | 97 |
| Syncephalastrum nigricans HUT 1299 | 35 | 98 |
| Tyromyces palustris IFO 30339 | 31 | 100 |
| Zygosporium masonii IFO 30214 | 40 | 99 |
| Gongranella butleri IFO 8080 | 32 | 100 |
| Achromobacter xerosis IFO 12668 | 40 | 70 |
| Agrobacterium radiobacter IFO 13259 | 32 | 73 |
| Bacillus pumilus IFO 3813 | 50 | 94 |
| Cellulomonas flavigena IFO 3748 | 39 | 62 |
| Citrobacter freundii IFO 12681 | 44 | 83 |
| Corynebacterium xerosis IFO 12684 | 45 | 79 |

TABLE 3

| Microorganisms | (S)-1,2-pentanediol | |
|---|---|---|
| | Yield* (%) | Optical purity (% e.e.) |
| Escherichia coli IFO 3301 | 37 | 73 |
| Microbacterium lacticum IFO 14135 | 43 | 78 |
| Pseudomonas chlororaphis IFO 3904 | 41 | 64 |
| Serratia marcescens IFO 12648 | 33 | 88 |
| Klebsiela pneumoniae IFO 3319 | 30 | 85 |
| Enterobacter cloacae IFO 12937 | 35 | 83 |
| Erwinia herbicola IFO 12686 | 28 | 76 |
| Hafnia alvei IFO 3731 | 31 | 65 |

*Yield = (Remaining 1,2-pentanediol/added 1,2-pentanediol) × 100

EXAMPLE 2

(A) Medium for yeasts Glucose 4%, $(NH_4)_2HPO_4$ 1.3%, $KH_2PO_4$ 0.7%, $MgSO_4.7H_2O$ 800 ppm., $ZnSO_4.7H_2O$ 60 ppm., $FeSO_4.7H_2O$ 90 ppm., $CuSO_4.5H_2O$ 5 ppm., $MnSO_4.4H_2O$ 10 ppm., NaCl 100 ppm., yeast extract 0.3%.

(B) Medium for molds Glucose 2%, meat extract 0.5%, peptone 0.5%, yeast extract 3%.

Each medium of the aforesaid composition was prepared using tap water (pH 7.0), poured into 500 ml Sakaguchi flasks 50 ml each and sterilized for 20 min. at 120° C.

The medium A was inoculated with each of the microorganisms shown in Table 5, and cultivated at 30° C. for 24–48 hours.

To the culture solution obtained, 500 mg or (R,S)-1,2-pentanediol was added and, after adjustment of its pH to 6.5, 1.0% glucose was added and reaction was allowed to proceed for 48 hours under shaking at 30° C.

Then, under saturation with ammonium sulfate extraction was repeated 3 times using 50 ml of ethyl acetate each time, and the organic layer was analyzed by the aforementioned GLC and the amount of 1,2-pentadiol was determined. And after subsequent dehydration with sodium sulfate anhydride and removal of the solvent, brown-colored oily 1,2-pentanediol was obtained. This was caused to react with p-toluene sulfonylchloride in methylene chloride in the presence of pyridine for synthesis of 2-hydroxypentyl-p-toluenesulfonate, this was analyzed by HPLC by the use of Chiral CEL CD (of Nippon Bunko, Ltd.) (eluting solution hexane-isopropanol (97:3), flow rate 0.7 ml/min., detection 254 nm, (S)-isomer was eluted in 50 minutes and (R)-isomer in 45 minutes), and the result of measuring optical purity of (S)-1,2-pentanediol [{(area of (S)-isomer)-(area of (R)-isomer)}/{(area of (S)-isomer)+(area of (R)-isomer)} × 100] is given in Tables 4 and 5, which show that optically-active (S)-1,2-pentanediol was obtained from (R,S)-1,2-pentanediol with a high yield.

By the way, none of the microorganisms used was confirmed to have ability to synthesize (R) and (S)-1,2-pentanediol directly from a hydrogen source such as glucose under the aforementioned conditions.

TABLE 4

| Microorganisms | (S)-1,2-pentanediol Yield* (%) | Optical purity (% e.e.) |
|---|---|---|
| Arthroascus javanensis IFO 1848 | 63 | 97 |
| Candida parapsilosis IFO 0585 | 75 | 100 |
| Candida maltosa ATCC 20275 | 73 | 98 |
| Debaryomyces hansenii IFO 0564 | 71 | 96 |
| Endomyces tetrasperma CBS 765.70 | 58 | 95 |
| Guilliermondella selenospora IFO 1850 | 55 | 94 |
| Lodderomyces elongisporus IFO 1676 | 77 | 100 |
| Pichia bovis IFO 0872 | 65 | 91 |
| Stephanoascus ciferrii IFO 1854 | 66 | 98 |

TABLE 5

| Microorganisms | (S)-1,2-pentanediol Yield* (%) | Optical purity (% e.e.) |
|---|---|---|
| Backusella circina IFO 9231 | 60 | 95 |
| Emericellopsis glabra IFO 9031 | 68 | 91 |
| Fusarium anguioides IFO 4467 | 73 | 98 |
| Gibberella fujikuroi IFO 6607 | 64 | 93 |
| Pholiota nameko IFO 30315 | 59 | 92 |
| Gongronella butleri IFO 8080 | 73 | 96 |
| Syncephalastrum nigricans HUT 1299 | 63 | 94 |
| Tyromyces palustris IFO 30339 | 55 | 98 |
| Zygosporium masonii IFO 30214 | 65 | 99 |

*Yield = (Remaining 1,2-diol/added 1,2-diol) × 100)

EXAMPLE 3

Each of the microorganisms listed on Table 6 and 7 was cultivated under the same conditions as in Example 2, 250 mg of (R)-1,2-pentadiol (100% e.e.) was added as substrate and, with pH adjusted to 6.5, reaction was allowed to proceed for 36 hours under shaking at 30° C. Then, extraction and analysis were made in the same way as the Example 2 and the results obtained were as seen from the Tables 6 and 7, steric inversion was clearly noted with each of the microorganisms tested.

By the way, none of the microorganisms used was confirmed to have ability to synthesize (R) and (S)-1,2-pentanediol directly from a hydrogen source such as glucose under the aforefmentioned conditions.

TABLE 6

| Microorganisms | (S)-1,2-pentanediol Yield* (%) | Optical purity (% e.e.) |
|---|---|---|
| Arthroascus javanensis IFO 1848 | 45 | 97 |
| Candida parapsilosis IFO 0585 | 58 | 99 |
| Candida maltosa ATCC 20275 | 53 | 97 |
| Debaryomyces hansenii IFO 0564 | 43 | 93 |
| Endomyces tetrasperma CBS 765.70 | 25 | 95 |
| Guilliermondella selenospora IFO 1850 | 61 | 95 |
| Lodderomyces elongisporus IFO 1676 | 55 | 100 |
| Pichia bovis IFO 0872 | 33 | 94 |

TABLE 6-continued

| Microorganisms | (S)-1,2-pentanediol Yield* (%) | Optical purity (% e.e.) |
|---|---|---|
| Stephanoascus ciferrii IFO 1854 | 44 | 97 |

TABLE 7

| Microorganisms | (S)-1,2-pentanediol Yield* (%) | Optical purity (% e.e.) |
|---|---|---|
| Backusella circina IFO 9231 | 32 | 91 |
| Emericellopsis glabra IFO 9031 | 41 | 83 |
| Fusarium anguioides IFO 4467 | 35 | 97 |
| Gibberella fujikuroi IFO 6607 | 37 | 94 |
| Pholiota nameko IFO 30315 | 34 | 90 |
| Gongronella butleri IFO 8080 | 63 | 98 |
| Syncephalastrum nigricans HUT 1299 | 27 | 95 |
| Tyromyces palustris IFO 30339 | 24 | 95 |
| Zygosporium masonii IFO 30214 | 36 | 93 |

*Yield = (Remaining 1,2-diol / added 1,2-diol) × 100

EXAMPLE 4

On the same medium (A) as in Example 1 Candida parapsilosis IFO 0585 and Lodderomyces elongisporus IFO 1976 were cultivated under shaking for 24 hours at 30° C., after subsequent addition of (R, S)-1,2-butanediol, (R, S)-1,2-hexanediol and (R, S)-1,2-heptanediol 500 mg each and, with pH adjusted to 6.5, reaction was conducted under shaking at 30° C. for the period shown in the table. Then extraction and analysis were made in the same way as described in Example 2 and obtained the results as shown in Table 8.

TABLE 8

| Microorganisms | | (S)-1,2-butanediol | (S)-1,2-hexanediol | (S)-1,2-heptanediol |
|---|---|---|---|---|
| Candida parapsilosis IFO 0585 | Reaction time (hrs) | 36 | 18 | 12 |
| | Yield* (%) | 62 | 78 | 82 |
| | Optical purity (% e.e.) | 95 | 99 | 100 |
| Loddermyces elongisporus IFO 1676 | Reaction time (hrs) | 36 | 18 | 12 |
| | Yield* (%) | 57 | 75 | 80 |
| | Optical purity (% e.e.) | 93 | 100 | 100 |

*Yield = (Remaining 1,2-diol/added 1,2-diol) × 100

EXAMPLE 5

On the same medium as in Example 2 Candida parapsilosis IFO 0585 and Lodderomyces elongisporus IFO 1676 were cultivated for 24 hours at 30° C. After subsequent addition of (R, S)-1-phenyl-1,2-ethanediol, (R, S)-3-phenol-1,2-propanediol and (R, S)-4-phenyl-1,2-butanediol 250 mg each and with adjustment of pH to 6.5, reaction was conducted for 48 hours under shaking at 30° C. After removal of the cells by centrifugation, the reaction product was extracted 3 times with ethyl acetate 50 ml each and the quantity thereof was determined by GLC and the concentrated product was analyzed by HPLC by the use of Chiral CEL OB (Nippon Bunko, Ltd.) (eluting solution, hexaneisopropanol (30:1), flow rate 1.3 ml/min., detection 254 nm, (R)-isomer is eluted in 40 minutes and (S)-isomer in the vicinity of 54 minutes) and, as seen from the data shown in Table 9, (S)-1-phenyl-1,2-ethanediol, (S)-3-phenyl-1,2- propanediol and (S)-4-phenyl-1,2-butanediol were obtained with high yield, respectively.

TABLE 9

| Microorganisms | (S)-1-phenyl-1,2-ethanediol | | (S)-3-phenyl-1,2-propanediol | | (S)-4-phenyl-1,2-butanediol | |
|---|---|---|---|---|---|---|
| | Yield* (%) | O.P. | Yield (%) | O.P. | Yield (%) | O.P(*) |
| Candida parapsilosis IFO 0585 | 96 | 98 | 71 | 83 | 97 | 85 |
| Lodderomyces elongisporus IFO 1617 | 95 | 96 | 65 | 78 | 94 | 82 |

*Yield = (Remaining 1,2-diol/added 1,2-diol) × 100
(*)O.P. = Optical purity (% e.e.)

What is claimed is:

1. A process for manufacturing optically active (S)-1,2-diols which comprises:
   (1) subjecting a racemic mixture of (R)-diols represented by the general formula (I):

     (I)

wherein R represents a substituted or unsubstituted alkyl group or alkenyl group, having from 2–6 carbon atoms and optically active (S)-1,2-diols represented by the general formula (II):

     (II)

wherein R represents the same as above, to the action of a microorganism capable of selectively metabolizing the (R)-diols (I) or capable of converting (R)-diols (I) into (S)-diols (II), or having both capabilities, and producing (S)-diols (II) in a yield exceeding 40% of the starting mixture,
   (2) said microorganism being selected from the group consisting of genera Arthroascus, Candida, Debaryomyces, Endomyces, Gilliermondells, Hansenula, Kluyveromyces, Lodderomyces, Pichia, Phodotorula, Saccharomyces, Stephanoascus, Trigonopsis, Achromobacter, Bacillus, Citrobacter, Corynebacterium, Microbacterium, Pseudomonas, Backsella, Cephalosporium, Circinella, Dicranidion, Emericellopsis, Fusarium, Gibberella, Gloeophyllum, Pholiota, Gongranella, Rhincolsdiella, Rhizopus, Syncephalastrum, Tyromyces and Zygosporium, and
   (3) collecting the formed and accumulated (S)-1,2-diols (II).

2. The process according to claim 1, wherein said microorganism capable of selectively metabolizing the (R)-diols (I) is selected from the group consisting of Arthroascus javanensis, Candida parapsilosis, Candida maltosa, Debaryomyces hansenii, Endomyces tetrasperma, Guilliermondells selenospora, Hansenula holstii, Klluyveromyces fragilis, Lodderomyces elongiosporus, Pichia toletana, Rhodotorula minuta, Saccharomyces bailii, Stephanoascus ciferrii, Trigonopsis variablis, Achromobacter xerosis, Bacillus pumilus, Citrobacter freundii, Corynebacterium xerosis, Microbacterium lacticum, Pseudomonus chlororaphis, Backsella circina, Cephalosporium potronii, Circinella mucoroides, Dicranidion fragile, Emericellopsis glabra, Fusarium anguioides, Gibberella fujikuroi, Gloeophyllum striatum, Pholiota nameko, Gongranella butleri, Rhincolsdiella anceps, Rhizopus stolonifer, Syncephalastrum nigricans, Tyromyces palustris and Zygosporium masonii.

3. The process according to claim 1 or 2, wherein said racemic mixture is butanediol, 1,2-pentanediol or 1,2-hexanediol.

4. A process for manufacturing optically active (S)-1,2-diols which comprises:
   (1) subjecting a racemic mixture of (R)-diols represented by the general formula (I):

     (I)

wherein R represents a substituted or unsubstituted alkyl group or alkenyl group, having from 2 to 6 carbon atoms and optically active (S)-1,2-diols represented by the general formula (II):

     (II)

wherein R represents the same as above, to the action of a microorganism and converting (R)-diols (I) into (S)-diols (II) in a yield exceeding 40% of the starting mixture.
   (2) said microorganism being selected from the group consisting of genera Arthrosacus, Candida, Debaryomyces, Endomyces, Guilliermondells, Lodderomyces, Pichia, Stephanoascus, Backsella, Emericellopsis, Fusarium, Gibberella, Pholiota, Syncephalastrum, Tyromyces, Zygosporium and Gongranella, and
   (3) collecting the formed and accumulated (S)-1,2-diols (II).

5. The process according to claim 4, wherein said microorganism is selected from the group consisting of Arthroascus javanensis, Candida parapsilosis, Candida maltosa, Debaryomyces hansenii, Endomyces tetrasperma, Guilliermondells selenospora, Lodderomyces elongiosporus, Pichia hobis, Stephanoascus ciferrii, Backsella circina, Emericellopsis glabra, Fusarium anguioides, Gibberella fujikuroi, Pholiota nameko, Gongranella butleri, Syncephalastrum nigricans, tyromyces palustria and Zygosporium masonii.

6. A process for manufacturing optically active (S)-1,2-heptanediol, (S)-1-phenyl-1,2-ethanediol, (S)-3-phenyl-1,2-propanediol or (S)-4-phenyl-1,2-butanediol which comprises:
   (1) subjecting a racemic mixture of said diol to the action of a microorganism capable of selectively metabolizing or capable of converting the (R)-diol of said racemic mixture into (S)-diol, or having both capabilities,
   (2) said microorganism being selected from the group consisting of genera Arthroascus, Candida, Debaryomyces, Endomyces, Guilliermondells, Hansenula, Kluyveromyces, Lodderomyces, Pichia, Rhodotorula, Saccharomyces, Stephanoascus, Trigonopsis, Achromobacter, Bacillus, Citrobacter, Corynebacterium, Microbacterium, Pseudomonas, Backsella, Cephalosporium, Circinella, Dicranidion, Emericellopsis, Fusarium, Gibberella, Gloeophyllum, Pholiota, Gongranella, Rhincolsdiella, Rhizopus, Syncephalastrum, Tyromyces and Zygosporium and
   (3) collecting the formed and accumulated said (S)-1,2-diol.

* * * * *